(12) United States Patent
Anderson

(10) Patent No.: US 7,838,515 B2
(45) Date of Patent: Nov. 23, 2010

(54) FORMULATIONS OF QUATERNARY AMMONIUM NEUROMUSCULAR BLOCKING AGENTS

(75) Inventor: David M. Anderson, Ashland, VA (US)

(73) Assignee: Lyotropic Therapeutics, Inc., Ashland, VA (US)

(*) Notice: Subject to any disclaimer, the term of this patent is extended or adjusted under 35 U.S.C. 154(b) by 1080 days.

(21) Appl. No.: 11/404,109

(22) Filed: Apr. 14, 2006

(65) Prior Publication Data

US 2006/0234989 A1 Oct. 19, 2006

Related U.S. Application Data

(60) Provisional application No. 60/671,455, filed on Apr. 15, 2005.

(51) Int. Cl.
*A61K 31/58* (2006.01)
*A61K 31/425* (2006.01)
*A61K 31/14* (2006.01)
*A01N 43/78* (2006.01)
*A01N 33/12* (2006.01)

(52) U.S. Cl. .................. 514/176; 514/372; 514/642

(58) Field of Classification Search ............... 514/176, 514/642, 372
See application file for complete search history.

(56) References Cited

U.S. PATENT DOCUMENTS 2,600,539 A * 6/1952 Jenesel et al. ............. 546/35
3,138,528 A 6/1964 Marcus 2003/0022242 A1 1/2003 Anderson
2005/0119340 A1 * 6/2005 Anderson et al. .......... 514/535

FOREIGN PATENT DOCUMENTS

EP 0008824 A1 * 3/1980
WO WO 00/44334 8/2000

OTHER PUBLICATIONS

Bhatt et al. "Saccharin as a salt former. Enhanced solubilities of saccharinates of active pharmaceutical ingredients" Chem. Comm., Jan. 12, 2004, vol. 8, pp. 1073-1075.*
Drummond et al. "Surfactant self-assembly objects as novel drug delivery vehicles" Current Opinion in Colloid & Interface Science 4, 2000, pp. 449-456.*
Cohen et al. "Studies of d-tubocurarine with measurements of concentration in human blood", Anesthesiology, Mar./Apr. 1957, vol. 18, issue 2, pp. 300-309.*
Nema, PDA Journal of Pharmaceutical Science & Technology, (1997) 51:166-1671.
Gould, International Journal of Pharmaceutics, (1986) 33:201-217.
Product description for Tracrium injection dated Oct. 3, 2000, pp. 1 to 14.

* cited by examiner

*Primary Examiner*—Sreeni Padmanabhan
*Assistant Examiner*—Kendra D Carter
(74) *Attorney, Agent, or Firm*—Whitham, Curtis, Christofferson & Cook, P.C.

(57) ABSTRACT

Muscle relaxant formulations which include one or more quaternary ammonium neuromuscular blocking agents have a reduced tendency for hydrolytic degradation, and therefore a longer shelf life stability, when combined with one or more organic anions having at least six carbon atoms and having a pKa of less than 4.0 (preferably ranging from 0.5 to 3.5). Particularly good results are achieved when using acids of very low solubility in water, such as gentisic acid which is less than 1% soluble at room temperature.

5 Claims, No Drawings

FORMULATIONS OF QUATERNARY AMMONIUM NEUROMUSCULAR BLOCKING AGENTS

This application claims priority to U.S. Provisional Application No. 60/671,455 filed Apr. 15, 2005.

BACKGROUND OF THE INVENTION

1. Field of the Invention

The present invention generally relates to formulations of quaternary ammonium neuromuscular blocking agents such as vecuronium, rocuronium, pancuronium, etc. which are used as skeletal muscle relaxants, for endotracheal tube insertion, and for other applications, where the formulations are designed to be water-continuous, low viscosity, safe for injection, and ready to use, but where contact between water and the hydrolyzable groups on the drug are limited so as to reduce the rate of hydrolysis and improve stability and shelf life.

2. Background Description

Salts of quaternary ammonium compounds such as vecuronium, rocuronium and pancuronium are currently used as skeletal muscle relaxants, and are generally given by intravenous injection prior to intubation, for example. Their rapid onset and short-acting behavior are key features to the success of these drugs. In the case of vecuronium bromide, a dose of 0.08 to 0.1 mg/Kg generally produces first depression of twitch response, under balanced anesthesia, in approximately 1 minute, with good or excellent intubation conditions within 2.5 to 3 minutes, with recovery 95% complete within 45 to 65 minutes.

However, many of the active pharmaceutical compounds in this class, and especially the marketed vecuronium and pancuronium formulations, are hydrolytically unstable, with rocuronium being rather more stable. In particular the acetate ester groups hydrolyze over time in aqueous solution, thereby potentially reducing efficacy, impacting safety, and limiting shelf life. Three methods have been used to limit this hydrolysis, each of which has distinct drawbacks and/or limitations. One method is to lower the hydrolysis rate by storing the product at refrigerator temperatures, as opposed to ambient. This method significantly increases the cost, and reduces convenience, for any of these compounds, and at least in the most unstable compounds in the class, such as vecuronium bromide, only extends room temperature shelf life by less than about 6 months. Another method is to formulate the product as an aqueous solution at low pH which reduces the hydrolysis rate. For example, a formulation of pancuronium bromide has been marketed by Gensia-Sicor Pharmaceuticals which has a pH of 3.8-4.2. Two problems result from this acidic pH: stinging upon injection, and a tendency to induce dangerous precipitation of other drug formulations administered in conjunction with the muscle relaxant, in particular sedatives such as thiopental sodium. In addition, the above two methods still do not solve the hydrolysis problem but only lengthen the shelf-life moderately. A third method is to formulate the drug as a reconstitutable powder, to which water for injection is added just prior to use. This introduces another step in the surgeon's or anesthesiologist's regiment, so is undesirable for that reason alone. In addition, such reconstitutable formulations must typically be sterilized by expensive gamma irradiation sterile fill procedures. Furthermore, in the event that not all the drug is re-dissolved or re-dispersed during the pre-injection step, this could lead to dangerous emboli, such as pulmonary emboli.

Quaternary ammonium skeletal muscle relaxants have in common a unique combination of structural and physicochemical characteristics that make their incorporation into a stable formulation challenging. To begin with, they have at least one (and in the case of pancuronium, for example, two) permanent cationic charge(s) (quaternary ammonium), giving the molecule a positive charge at essentially all values of pH, and certainly at all values of pH relevant to drug delivery. Since nearly all pharmaceutically acceptable ionic surfactants are anionic, the presence of a drug with a cationic charge will act to reduce the magnitude of the zeta potential for virtually any type of particle or droplet. This can render conventional attempts to achieve electrostatic stabilization ineffective, or cause required levels of surfactant to increase significantly, thus exacerbating their undesirable effects. A second characteristic shared by these compounds is a significant hydrophobic moiety within the molecule, typically a 19-carbon steroidal ring system (counting the side methyl groups), which nonetheless does not yield a high octanol-water partition coefficient for the drug. This is a major hurdle for many common formulation schemes for protecting active compounds from water contact. Since octanol-water partition coefficients of the entire class of quaternary ammonium skeletal muscle relaxants will generally be quite low, less than 1.0 (i.e., low Kow<0), this tends to teach away from the use of lipid-based vehicles in attempting to reduce water-drug contact for these compounds. In addition, the solubility of these drugs in glycerol and other injectable solvents is generally very low. Hence, drugs in the quaternary ammonium neuromuscular blocking agent class possess a combination of characteristics that intertwine and make the formulation of such a compound in a protective milieu very challenging.

SUMMARY OF THE INVENTION

In an exemplary embodiment of the invention, quaternary ammonium skeletal muscle relaxants (or other neuromuscular blocking agents), are formulated to have improved stability and shelf-life in an aqueous formulation that is ready-to-use and does not require reconstitution, and is pharmaceutically acceptable for intravenous injection.

According to the invention, a high degree of partitioning of the drug into a protective, and in particular, hydrophobic or amphiphilic, milieu has been found to be a very effective measure for limiting hydrolytic decomposition of the drug, due most likely to the limited contact between water and the hydrolytically labile group(s) on the drug molecule when that group is in a hydrophobic domain or local milieu. Certain additives have been found to be surprisingly effective at improving drug stability. These additives are organic anions with 6 or more carbon atoms (for establishing a sufficiently hydrophobic milieu), and pKa's of less than 4, i.e., in the range of about 0.5-3.5 preferably, and more preferably in the range of about 1.5-3.0, for electrostatic binding or association with the cationic group or protonated group of the drug molecule (and displacement of offensive hydroxyl ions). These additives may be in the form of an acid which has a water solubility of 5% or less in its acid (protonated) form, in pure water. For example, gentisic acid, one of the most preferred compounds of this invention, is less than 1% soluble in water at room temperature as an acid; although it is quite soluble in salt form, that does not figure into this solubility criterion, for the purposes of this disclosure. Also for the purposes of this invention, we will refer to the acid and salt (or "anion") forms interchangeably when discussing properties, since the relative amounts of acid (protonated) and anion (salt, or deprotonated) forms are easily calculated from the pKa and formulation pH by a formula well known to anyone in the art. Particularly good results are achieved using gentisic acid, benzenesulfonic acid, and/or saccharin, alone or in combination. The Examples herein demonstrate that vecuronium chemical stability against hydrolysis is greatly enhanced by this particular class of additives at the concentrations discussed herein, while other additives that do not satisfy these criteria are either much less effective as stabilizers, or in fact (as in the case of acetic acid) actually accelerate degradation of the drug.

In this invention, the drug-stabilizing organic anions, taken together, will generally be at a significant molar excess to the drug—or more precisely, to the moles of cationic groups (usually quaternary ammonium groups) on the drug molecules. That is, in cases, such as pancuronium, where the drug has more than one cationic group, the molar ratio should be calculated as the total number of moles of the organic anion or anions, divided by the total number of moles of cationic groups on the drug molecules; the latter is calculated by multiplying the number of moles of drug by the number of cationic groups per molecule, which is usually either one or two. The preferred molar excess (calculated by subtracting unity from this molar ratio and multiplying by 100%) will preferably be greater than or equal to about 100% (i.e., molar ratio of 2:1), and more preferably greater than or equal to about 200%, and in the case of vecuronium most preferably greater than about 800%, with the exception of organic anions with 10 or more carbons where the preferred ratio can be anything from zero (no excess) or above. Without wishing to be bound by theory, it is believed that a 100% molar excess or more has the best chance of displacing both the nominal counterion of the drug (bromide, chloride, etc.) and any hydroxyl ions bound to the cationic group or other basic (viz., amino) groups on the molecule.

Although as just noted several drugs in this class have more than one cationic (quaternary ammonium) group, increasingly the monoquaternary representatives of the class, such as vecuronium, are more strongly preferred for clinical use since they have fewer cardiovascular side effects and better kinetics. Monoquaternary drugs of this class are preferred in the instant invention, with vecuronium being especially preferred.

As is discussed in more detail herein, certain organic anions which possess a synergistic combination of hydrophobicity and carefully selected pKa are remarkably effective drug-stabilizing excipients for the quaternary ammonium neuromuscular blocking agent class of drugs, when incorporated in organic salt form either with a base or with the cation form (i.e., counterion-free) of the drug, or in solutions or in dispersions of the drug. For example, the addition of gentisic acid ethanolamine has a powerful drug-stabilizing effect even at concentrations of 2 or 3%. Significantly, gentisic acid ethanolamine has a history of safe use in intravenous drug formulations, as do benzenesulfonate and saccharin. Without wishing to be bound by theory, the range of pKa found to be required of the organic ion in order to serve as a drug-stabilizing excipient, namely about 0.5-3.5, or more preferably 1.5-3.0, is believed to be because the acid needs to be strong enough to displace hydroxyl groups associated with the drug molecule, but acids too strong would be less tightly bound to the quaternary ammonium group on the drug. Thus, the pKa of gentisic acid (gentisate), the most preferred acid (anion), is about 2.9, making it lower than the pKb of typical drugs in this class, but not so low that the isolated, free anion form of the gentisate is energetically favorable (in hydrated form, of course). As an example of the need for a pKa greater than about 0.5, a molar excess, and a sufficiently high carbon number, consider that the pKa of hydrobromic acid (HBr) is about −9 (negative 9), and that the highly instable vecuronium bromide molecule can be regarded as an equimolar product of HBr with vecuronium. More evidence for the need of a molar excess of anions is provided by one of the Examples below in which the amino acid glycine is incorporated at a huge molar excess to vecuronium bromide, but because each molecule of glycine introduces one positively-charged group as well as one anion, the net result of adding a zwitterionic compound is not the same as that accomplished by addition of a molar excess of a simple anion.

A hydrophobic group on the anion, such that the anion has at least 6 carbon atoms most preferably in a contiguous hydrophobic group, can improve binding of, or association of, the anionic compound with the cationic drug and subsequent stabilization by a combination of one or more effects, including: A) a hydrophobic interaction with the hydrophobic portion of the drug (which is of considerable MW in drugs of this class); B) a reduced translational entropy and thus tighter binding to drug due to higher molecular weight than, say, an atomic cation or an amino acid; C) the creation of a sufficiently hydrophobic local environment (or "milieu") around the drug, particular at the site of the labile group, upon associating with the drug and/or with other anions associated with the drug; and D) a reduced partitioning into water domains, in systems comprising water-lean domains by virtue of other additives.

In short, there can be a synergy between the anion-drug charge interaction, and these interactions owing to the hydrophobic group(s) on the anion, and in turn this can be additive or synergistic with hydrophobizing/water-excluding effects of other additives or lipid matrices. The latter can include one or more of the following. First, chaotropic agents (or "chaotropes") such as guanidine, urea, or thiocyanate ions can be used to, in a sense, make the water "more hydrophobic" by disrupting hydrogen bonds between water molecules. Second, polyethyleneglycols (PEG compounds) or less preferably glycerol can be incorporated, which are water-soluble yet fairly hydrophobic, increasingly so as temperature increases in the preferred case of PEG; the preferred concentration of PEG is between about 15 and 40% by weight. And third, lipid or surfactant microstructures can be invoked, as illustrated by a number of the Examples below in which particles of reversed lyotropic liquid crystalline phase materials, namely reversed cubic phase and reversed hexagonal phase materials, the preferred microstructured components, are incorporated and provide hydrophobic domains that are water-lean and thus more benign toward hydrolytically unstable groups. As is shown in the Examples, incorporation of one of the preferred anions of this invention can actually drive the drug molecule, by virtue of the association with the hydrophobic anion and tight ion-pairing, into the hydrophobe-rich particles (as quantified by the partition coefficient measured between the particle matrix and water), thus revealing a beneficial synergy between drug-anion charge interactions, drug-anion hydrophobic interactions, and three-way drug-anion-particle interactions.

Concerning the anionic compounds of utility in this invention, compounds with only one or two anionic groups are preferred, and those with only one anionic group being especially preferred, where an ionizable group is to be considered anion only when it has a pKa less than about 7, in accordance with the discussion above. That is, in the formulations of this invention, the pH will be such that an acid with a pKa above about 7 will not be ionized in the formulation. With compounds having more than one anionic group, the number of carbons should, in the context of this invention, be calculated by dividing the number of carbons by the number of anionic groups. Thus, for example, with the compound EDTA (ethylene diamine tetracetic acid), the number of carbons, 10, is divided by the number of anionic groups, which in view of the pKa's is 3 (the values are pKa1=2.0, pKa2=2.7, pKa3=6.2, and pKa4=10.0).

DETAILED DESCRIPTION OF A PREFERRED EMBODIMENT OF THE INVENTION

The preferred pharmaceutical ingredients for the present invention are those belonging to the class of non-depolarizing skeletal muscle relaxants, and most preferred are the quaternary ammonium steroidal blocking agent compounds in that class which include, without limitation, the salts of vecuronium, rocuronium, alcuronium, decamethonium, rapacuronium, pancuronium, 3-deacetylpancuronium, 3-deacetylvecuronium, pipecuronium, rocuronium, and 3-deacetylpipecuronium. Other quaternary ammonium compounds in the class of non-depolarizing skeletal muscle relaxants include salts of atracurium, benzoquinonium, doxacurium, mivacurium, C-calebassine, decamethonium, fazadinium, gallamine, hexacarbacholine, hexafluorenium, laudexium, leptodactyline, metocurine, and tubocurarine. Each of these muscle relaxant compounds has a quaternary ammonium cationic group (or atom, strictly speaking), and a significant hydrophobic moiety, particularly those with a steroidal backbone. Those which also are hydrolytically unstable, due to the presence of hydrolysis-prone groups such as esters (usually acetate esters), are of particular focus in this disclosure, with vecuronium being especially important due to its rapid decomposition by ester hydrolysis. The steroidal compounds in this class in particular have hydrolysable esters directly attached to the steroidal backbone, which makes the invention particularly effective due to the hydrophobic interaction between the steroidal backbone and the organic anions of the invention, since this interaction promotes a more intimate association between the organic anion and the hydrolysable group, and thus protection of the latter, in the case of a steroidal drug.

In the practice of this invention, the quaternary ammonium neuromuscular blocking agent will be combined with one or more organic anions with six or more carbon atoms, and a pKa ranging from 0.5-3.5 (more preferably 1.5-3.0). It has been found that each of these organic anions serves as a stabilizing agent which limits hydrolytic decomposition of the drug, most likely by limiting contact of the hydrolytically labile groups on the drug with water. The molar excess of organic anion(s) to drug (or actually to cationic groups of the drug molecules, as defined above) is preferably greater than or equal to about 100%, more preferably greater than or equal to about 200%, and in the case of vecuronium most preferably greater than or equal to about 800%, with the exception of organic anions with 10 or more carbons where no molar excess is required. Gentisic acid, benzenesulfonic acid, and saccharin are particularly preferred organic anions in the practice of this invention; however, a number of other agents, which are pharmaceutically-acceptable for injection, may also be used so long as they function to create a hydrophobic milieu for the hydrolytic moiety of the pharmaceutical active. Examples of other suitable organic anions include glycocholate, N-acetyltryptophanate, diacylphosphatidylglycerol, toluenesulfonic acid, and tocopherol phosphate.

Because the drugs of this class are usually alkaline in aqueous solution, addition of the additive in acid form (the "protonated organic anion", so to speak) will result in the first portion of this acid being deprotonated by the drug. Beyond this, and depending on the desired formulation pH, additional base is generally required, both to avoid undesirably low pH and to put the organic additive in its higher-solubility, salt form. Preferred bases for accomplishing this are described herein, with sodium or potassium hydroxide, piperidine, and ethanolamine being the most preferred. Indeed, it was found in the course of this work that as the number of hydroxyl groups on the base increases, it becomes less favorable in terms of drug stabilization, and that simple bases are favored over basic amino acids; preferred bases have at most one hydroxyl group per molecule. Ethanolamine is a preferred base, together with the alkali hydroxides. Piperidine is more effective in terms of stabilizing the drugs of this class, but does not have a history of safe use in injectable products, so is less favored than ethanolamine from that perspective.

The combination of drug and anion will preferably be formulated in a liquid carrier. However, formulation in a matrix material such as a pill, tablet, or lozenge may also be performed. If in liquid form, the drug and anion may be in solution, or in the form of a dispersion (e.g., emulsion). Also, the formulation may be incorporated into particles comprising lyotropic liquid crystalline materials (see, for example, U.S. Pat. No. 6,991,809 to Anderson, U.S. Pat. No. 6,989,195 to Anderson, U.S. Pat. No. 6,638,621 to Anderson, U.S. Pat. No. 6,482,517 to Anderson, U.S. Patent Publication 20050077497 to Anderson, and U.S. Patent Application 20040156816 to Anderson, all of which are herein incorporated by reference). Due to the presence of the organic anion, the active pharmaceutical ingredient (API) experiences less hydrolytic breakdown during storage and therefore has an extended shelf life. For many of the muscle relaxants contemplated by this invention, storage will be at a refrigerator temperature. However, it will be understood that the invention improves room temperature stability. Furthermore, the pH of the muscle relaxant formulations will be at or near physiologic. While at low pH (e.g. pH 4) one may get improved stability, the pain on injection increases at these acidic pH conditions. A variety of other compounds may also be included within the compositions of the present invention including chelating agents, buffers, etc. A high purity of water, very low in heavy metal contaminants, is crucial for stability in this invention.

Preferred embodiments of this invention are "ready-to-use" formulations that do not require addition of a component, such as water (WFI), nor prolonged (viz., longer than 15 seconds) shaking, prior to injection. The need for such a measure, in the context of a surgical or ambulatory procedure, introduces not only complication and inconvenience but also dangers, in the form of possible contamination and injection of undissolved particulate matter. By incorporating the drug, excipients (including one or more organic anions as per the invention), and in some cases particles, in a liquid carrier, which most preferably comprises water-for-injection, these embodiments can be supplied as ready-to-use formulations that do not require reconstitution.

These pharmaceuticals will be provided to patients, both man and animal, that are in need of a muscle relaxant. Examples include human subjects in need of temporary paralysis for the purposes of intubation, or human subjects in need of surgery or mechanical ventilation. These pharmaceuticals may be provided alone or in combination with other pharmaceuticals (e.g., anesthetics, etc.). These pharmaceuticals will preferably be administered by injection (e.g., i.p., i.v., i.m., subQ, etc.), or by other routes (oral, intranasal, buccal, transdermal, rectal, intraocular, etc.), with intravenous being most preferred. Preferably the formulations will be in liquid form; however, the formulations may also be administered as a tablet, pill, lozenge, capsule, transdermal patch, etc. The less acidic pH of the present formulations, as compared to commercially available formulations which do not take advantage of the water starving excipient milieu described herein (e.g., the presence of hydrophobic domains and an extended polar-apolar interface), can reduce the risk of precipitation when the formulation is administered in conjunction with another formulation, for example, a sedative such as thiopental sodium or a relative thereof. Liquid dispersions of the pharmaceuticals as described herein will allow delivery via a catheter (bolus dosing, maintenance dosing, continuous infusion, etc.).

EXAMPLES

In the Examples below, where HPLC assay results for vecuronium are reported, the following gives the parameters of the HPLC measurement. HPLC System was a Shimadzu VP Series that consists of the following components: SPD-M10A—Diode Array Detector; SIL-10AD—Autosampler; LC-10AT—Pump; SCL-10A—Controller; and Shimadzu EZ Start Version 7.2 SP 1 Revision B—Software. Chromatographic Parameters: Mobile Phase—60% Acetonitrile, 25% Methanol, 15% 0.1M TMAH (pH=6.5); Column—25 cm×4.6 mm Phenomenex Luna C18 5 µm; Wavelength—210 nm; Injection Volume—5 µL; Flow Rate—1.0 mL/min; Standard Preparation—1 mg/mL in 0.001N HCl/Methanol; and Sample Preparation—1 mg/mL—Undiluted.

According to samples of vecuronium bromide dissolved at 1 mg/ml in water, buffered to various pH values in the course of this work, the shelf-life, as defined above (namely the point at which 15% of the drug potency is lost) of these control solutions, is a function of the pH and temperature as follows:

| Drug | pH | Temp | shelf-life of solution |
|---|---|---|---|
| Vecuronium | 6.0 | 25° C. | 1 week |
| Vecuronium | 6.0 | 4° C. | 5 weeks |

In the case of vecuronium at pH 6 and 25° C., the shelf-life of just under 1 week was recorded for both a maleate-TRIS buffer and an HCl-acidified vecuronium solution.

Example 1

In this Example a number of anionic compounds, with various pKa's and carbon numbers, were compared for their ability to stabilize vecuronium in solution. In particular, the following anions (or acids, depending on titration state; herein both terms refer to these compounds) were investigated, where the pKa and carbon number have been listed:

| acid | carbons | pKa |
|---|---|---|
| toluenesulfonic | 8 | 0.7 |
| benzenesulfonic | 6 | 0.7 |
| saccharin | 7 | 2.0 |
| gentisic | 7 | 2.9 |
| N-acetyltryptophan | 13 | 3.4 |
| glycocholic | 26 | 3.5 |
| maleic | 4 | 3.9 |
| ascorbic | 6 | 4.1 |
| octanoic | 8 | 4.5 |
| acetic | 2 | 4.7 |
| cholic | 24 | 5.0 |

The following chart gives the compositions that were prepared and examined by HPLC for stability over time. Each sample contained approximately 1 mg/mL vecuronium bromide. Each sample was titrated to pH 6.0, except for the cholic acid and octanoic acid samples, which were titrated to pH 6.7 and 6.9, respectively; the sixth column in the chart gives the identity of the compound that was used to titrate the pH, the penultimate column gives the targeted concentration of the anion, and the right-most column gives the molar excess of organic anion to vecuronium. Similarly the first two entries are controls, with negligible amounts of acid in comparison to the majority of samples. All numerical entries in the chart are actual recorded weights in grams:

| # | Acid | Acid wt (gm) | Water (gm) | Vec-Br (gm) | Titrate with: | [Acid] % | Molar excess % |
|---|---|---|---|---|---|---|---|
| 1 | Hydrochloric | To pH 6 | 59.9 | 0.060 | Hydrochloric | — | — |
| 2 | Acetic | To pH 6 | 59.9 | 0.061 | Acetic | — | — |
| 3 | Gentisic | 1.801 | 58.2 | 0.061 | Ethanolamine | 3% | 12,000 |
| 4 | Gentisic | 0.603 | 59.2 | 0.062 | Ethanolamine | 1% | 3,000 |
| 5 | Gentisic | 0.015 | 59.9 | 0.062 | Ethanolamine | 1:1 | 0 |
| 6 | Benzenesulfonic | 1.80 | 58.1 | 0.063 | Ethanolamine | 3% | 11,500 |
| 7 | Benzenesulfonic | 0.60 | 59.1 | 0.063 | Ethanolamine | 1% | 3,700 |
| 8 | Benzenesulfonic | 0.025 | 59.0 | 0.063 | Ethanolamine | 1:1 | 0 |
| 9 | Gentisic | 1.804 | 58.1 | 0.063 | Ammonia | 3% | 12,000 |
| 10 | Benzenesulfonic | 1.80 | 58.1 | 0.063 | Ammonia | 3% | 11,500 |
| 11 | Toluenesulfonic | 1.981 | 55.0 | 0.062 | Ethanolamine | 3.5% | 11,800 |
| 12 | Maleic | 1.806 | 57.0 | 0.062 | Ethanolamine | 3% | 16,500 |
| 13 | Ascorbic | 1.804 | 57.0 | 0.060 | Ethanolamine | 3% | 11,000 |
| 14 | Glacial acetic | 1.805 | 57.0 | 0.060 | Ethanolamine | 3% | 32,000 |
| 15 | Glycine | 1.805 | 58.0 | 0.061 | Hydrochloric | 3% | 25,000 |
| 16 | Saccharin | 1.811 | 58.0 | 0.061 | Sodium hydroxide | 3% | 10,500 |
| 17 | Glycocholic | 0.600 | 58.9 | 0.062 | Sodium hydroxide | 1% | 1,200 |
| 18 | Cholic | 1.799 | 57.0 | 0.061 | Sodium hydroxide | 3% | 4,300 |
| 19 | Octanoic | 1.799 | 57.0 | 0.062 | Ethanolamine | 3% | 12,000 |
| 20 | N-acetyl tryptophan | 1.80 | 58.0 | 0.061 | Ethanolamine | 3% | 7,500 |

Samples were analyzed by HPLC for vecuronium potency, at the one-week or two-week point as indicated, and the results are given in the following table, with the last column given the concentration in mg/mL of vecuronium as determined by HPLC:

| Sample | Initial | 1 Week | 2 Weeks | 3 Weeks | 4 Weeks | 5 Weeks |
|---|---|---|---|---|---|---|
| #3 - REF | 1.11 | | 1.00 | 1.00 | 1.01 | 1.00 |
| #3 - RT | 1.11 | | N/A* | 0.774 | 0.744 | 0.710 |
| #3 - 40° C. | 1.11 | | N/A | 0.363 | 0.327 | 0.263 |
| #4 - REF | 1.09 | | 1.02 | 1.03 | 1.02 | 1.01 |
| #4 - RT | 1.09 | | 0.920 | 0.841 | 0.841 | 0.798 |
| #4 - 40° C. | 1.09 | | 0.606 | 0.497 | 0.455 | 0.391 |
| #5 - REF | 1.09 | | 1.01 | 0.986 | 1.02 | 1.00 |
| #5 - RT | 1.09 | | 0.897 | 0.820 | 0.807 | 0.742 |
| #5 - 40° C. | 1.09 | | 0.784 | 0.705 | 0.672 | 0.619 |
| #9 - REF | 0.904 | | 0.849 | 0.490 | 0.565 | 0.567 |
| #9 - RT | 0.904 | | 0.693 | 0.370 | 0.405 | 0.377 |
| #9 - 40° C. | 0.904 | | 0.371 | 0.148 | 0.158 | 0.102 |
| #6 - REF | 1.11 | | 1.05 | 1.03 | 1.04 | 1.04 |
| #6 - RT | 1.11 | | 1.02 | 1.01 | 1.00 | 0.981 |
| #6 - 40° C. | 1.11 | | 0.886 | 0.828 | 0.803 | 0.772 |
| #7 - REF | 1.09 | | 1.03 | 1.04 | 1.06 | 1.05 |
| #7 - RT | 1.09 | | 1.00 | 1.00 | 0.994 | 0.977 |
| #7 - 40° C. | 1.09 | | 0.944 | 0.853 | 0.827 | 0.792 |
| #8 - REF | 1.03 | | 1.00 | 0.973 | 0.992 | 0.957 |
| #8 - RT | 1.03 | | 0.903 | 0.768 | 0.725 | 0.600 |
| #8 - 40° C. | 1.03 | | 0.828 | 0.764 | 0.746 | 0.695 |
| #10 - REF | 1.07 | | 0.977 | 0.498 | 0.618 | 0.728 |
| #10 - RT | 1.07 | | 0.920 | 0.447 | 0.545 | 0.648 |
| #10 - 40° C. | 1.07 | | 0.820 | 0.371 | 0.465 | 0.524 |
| #1 - REF | 1.03 | | 0.929 | 0.961 | 0.948 | 0.921 |
| #1 - RT | 1.03 | | 0.907 | 0.861 | 0.791 | 0.627 |
| #1 - 40° C. | 1.03 | | 0.828 | 0.746 | 0.710 | 0.665 |
| #2 - REF | 1.05 | | 1.017 | 0.980 | 0.981 | 0.945 |
| #2 - RT | 1.05 | | 0.645 | 0.505 | 0.464 | 0.394 |
| #2 - 40° C. | 1.05 | | 0.139 | 0.051 | 0.027 | 0.012 |
| #20 - REF | 1.31 | | 1.18 | 1.16 | 1.18 | 1.14 |
| #20 - RT | 1.31 | | 0.910 | 0.786 | 0.731 | 0.652 |
| #20 - 40° C. | 1.31 | | 0.374 | 0.197 | 0.153 | 0.101 |
| #11 - REF | 0.981 | 1.04 | 1.02 | 1.14 | 0.990 | |
| #11 - RT | 0.981 | 1.02 | 1.00 | 0.978 | 0.943 | |
| #11 - 40° C. | 0.981 | 0.894 | 0.886 | 0.850 | 0.789 | |
| #14 - REF | 0.961 | 0.667 | 1.01 | 1.01 | 0.959 | |
| #14 - RT | 0.961 | 0.836 | 0.612 | 0.535 | 0.421 | |
| #14 - 40° C. | 0.961 | 0.181 | 0.029 | 0.019 | 0.000 | |
| #15 - REF | 0.952 | 0.979 | 0.940 | 0.931 | 0.881 | |
| #15 - RT | 0.952 | 0.828 | 0.686 | 0.648 | 0.579 | |
| #15 - 40° C. | 0.952 | 0.320 | 0.249 | 0.190 | 0.124 | |
| #13 - REF | 1.02 | 0.677 | 0.956 | 0.968 | 0.934 | |
| #13 - RT | 1.02 | 0.796 | 0.602 | 0.531 | 0.420 | |
| #13 - 40° C. | 1.02 | 0.244 | 0.052 | 0.026 | 0.008 | |
| #12 - REF | 1.03 | 0.986 | 0.985 | 0.979 | 0.958 | |
| #12 - RT | 1.03 | 0.931 | 0.611 | 0.588 | 0.484 | |
| #12 - 40° C. | 1.03 | 0.774 | 0.068 | 0.036 | 0.017 | |
| #17 - REF | 1.02 | 0.932 | 0.969 | 0.948 | 0.931 | |
| #17 - RT | 1.02 | 0.895 | 0.718 | 0.641 | 0.566 | |
| #17 - 40° C. | 1.02 | 0.503 | 0.258 | 0.177 | 0.117 | |
| #18 - REF | 0.978 | 0.837 | 0.738 | 0.694 | 0.551 | |
| #18 - RT | 0.978 | 0.401 | 0.117 | 0.055 | 0.006 | |
| #18 - 40° C. | 0.978 | 0.017 | 0.000 | 0.000 | 0.000 | |
| #16 - REF | 0.949 | 0.990 | 0.958 | 0.988 | 0.974 | |
| #16 - RT | 0.949 | 0.990 | 0.982 | 0.966 | 0.922 | |
| #16 - 40° C. | 0.949 | 0.940 | 0.852 | 0.803 | 0.741 | |
| #19 - REF | 0.838 | 0.660 | 0.611 | 0.629 | 0.463 | |
| #19 - RT | 0.838 | 0.030 | 0.033 | 0.016 | 0.008 | |
| #19 - 40° C. | 0.838 | 0.000 | 0.000 | 0.000 | 0.008 | |

*Two samples have no HPLC data available due to erroneous injection

Several points from the table are notable. First, focusing on the more differentiating 25° C. and especially 40° C. data, and making note of which are 1-week results and which are 2-weeks, clearly the most stable solutions are those with the following additives: saccharin, benzenesulfonic acid, toluenesulfonic, and gentisic acid. Second, acetic acid is very detrimental to stability, which is of particular importance because the prior art teaches the use of acetate as a buffer in solutions of these drugs. Octanoic acid, with a similar pKa (about 4.5) but much higher carbon number, is equally bad, indicating that the effect of the pKa is very strong, and in particular pKa must be less than 4, and preferably less than about 3.5, for any stabilizing effect, and indeed to avoid actually diminishing stability. It is clear that currently marketed formulations incorporating acetate buffer (or acetic acid) teach away from the instant invention. Without wishing to be bound by theory, it is possible that when the pKa of a carboxylic acid is near 4.5 (or greater) as it is in acetic and octanoic acids, at the pH's employed in these formulations a significant fraction of the acid is protonated and available for strong hydrogen bonding, which can effectively increase the polarity of the local milieu in the vicinity of the drug and/or promote the molecular collisions involved in hydrolysis. Third, concentrations of 3% additive are substantially more effective than 1:1 molar ratios.

In the above results, the most effective stabilizing acids have pKa's below about 3.5, namely gentisic (pKa 2.9), saccharin (2.0), and benzenesulfonic (0.7), whereas those with pKa's above about 3.5 are clearly less effective, namely maleic (3.9); ascorbic (4.1), cholic (5.0), and deoxycholic acid (pKa about 5.7); NAT, with it's pKa of 3.4, performed very poorly at the higher temperature, but this could simply be due to hydrolysis of the additive itself into tryptophan and acetic acid. Furthermore, the optimal pKa should be in the range of about 0.5-3.5, or more preferably 1.5-3.0, on the basis that while the acid needs to be strong enough to displace the hydroxyl ion on the drug, acids stronger than this (i.e., pKa<0.5, or <1.5) would be less tightly bound to the quaternary ammonium group on the drug.

To reiterate, in the instant invention, the most effective stabilizing compound is the organic salt of an organic anion with a hydrophobic group wherein the pKa of the anion is less than about 4, and preferably in the range of about 0.5-3.5, and most preferably in the range of about 1.5-3.0. In order for the hydrophobic character of the organic anion to be pronounced enough, the anionic compound should contain at least 6 carbon atoms. The hydrophobic group on the anion can improve binding of the anionic compound to the cationic drug by several effects, including a reduced partitioning into water domains, a hydrophobic interaction with the hydrophobic portion of the drug (which is of considerable MW), and a reduced translational entropy due to higher molecular weight than, say, an atomic cation or an amino acid. In short, there can be a synergy between the anion-drug charge interaction and these interactions owing to the hydrophobic group(s) on the anion.

Example 2

The stability-enhancing effects of aqueous polyethyleneglycols were examined by preparing solutions containing the various additives, and with vecuronium bromide in each sample at 1.0 mg/ml, and then comparing the amount of chemically intact (i.e., not degraded) vecuronium bromide at the end of one week of storage. Thus, HPLC analysis was performed on each sample on the day the mixtures were prepared, and at the one-week point. The degradation of vecuronium bromide is rapid enough that this is indicative of the stability-enhancing effects. Each sample was prepared in duplicate, with one stored at room temperature and the other in a refrigerator.

Results of HPLC assay for vecuronium bromide at one week, in solutions originally containing 1.0 mg/ml.

Refrigerated samples:
Control—0.322 mg/mL
0.05% EDTA—0.937 mg/mL
10% P85+3% Vitamin E—0.669 mg/mL
70/30 Glycerol/Water+EDTA—Unable to calculate a value; poor integration
60/40 PEG 3350/Water+EDTA—0.973 mg/mL
Room temperature samples:
Control—0.341 mg/mL
0.05% EDTA—0.814 mg/mL
10% P85+3% Vitamin E—0.508 mg/mL
70/30 Glycerol/Water+EDTA—0.486 mg/mL
60/40 PEG 3350/Water+EDTA—0.778 mg/mL HPLC results at the two-week time point.
Room temperature:
Control—0.329 mg/ml
0.05% EDTA—0.700 mg/mL
10% P85+3% Vitamin E—0.422 mg/mL
70/30 Glycerol/Water+EDTA—0.028 mg/mL
60/40 PEG 3350/Water+EDTA—0.835 mg/mL
Refrigerated samples:
Control—0.127 mg/ml
0.05% EDTA—0.456 mg/mL
10% P85+3% Vitamin E—0.283 mg/mL
70/30 Glycerol/Water+EDTA—None Detected
60/40 PEG 3350/Water+EDTA—0.542 mg/mL These results demonstrate that vecuronium stability can be substantially increased by the addition of polyethyleneglycol (PEG). PEG 3350 has the additional advantage that it does not strongly increase osmolality, because of its high molecular weight. This additive was more effective than reduced temperature, and some of the measures reduced the amount of decomposition by more than about 3-fold (i.e., more than 67%) at room temperature, and more than about 10-fold (90%) at refrigerator temperature (at the one-week point). The surprising result reported in this experiment, namely that room temperature stabilities appear to be comparable to those at refrigerator temperatures, is due in part to the inverse temperature dependence of PEG, and of PEGylated surfactants. In particular, as temperature is increased, PEG-rich domains form which can be protective of the drug.

Example 3

The organic anion glycocholate was shown to improve stability of vecuronium in this Example. A reversed cubic phase containing the quaternary ammonium steroidal neuromuscular blocking agent vecuronium bromide was prepared by first dissolving 0.111 grams of vecuronium bromide (ChemPacific) in 1.283 gm of 0.01N hydrochloric acid (Aldrich). Upon dissolution, 1.270 gm of vitamin E and 2.859 gm of Pluronic L122 (Ethox) were added. After thorough mixing, the material was optically isotropic and of high viscosity. Next, a 1.36% sodium glycocholate solution was prepared by mixing 0.217 gm of the anionic surfactant glycocholic acid hydrate (Sigma), 0.474 gm of 1.0N sodium hydroxide, and 15.317 gm of distilled water. Glycocholic acid has a pKa of approximately 3.5 (at the concentration used here), and 26 carbon atoms.

Then, 0.301 gm of glycine (Spectrum) was dissolved in 14.698 gm the 1.36% sodium glycocholate solution. An amount 4.990 gm of the cubic phase was then added to the surfactant solution and dispersed, first using a homogenizer (Brinkmann Polytron PT3000) at 29.5 k RPM for 1 minute, then using a microfluidizer at 18 kpsi for four runs of 1.5 minutes each. The vecuronium bromide dispersion was pH adjusted from 7.3 to 5.2 using glacial acetic acid (Spectrum Chemical Company, Gardena, Calif.). The dispersion was then filtered using a 0.22 μm PVDF syringe filter (Millipore, Ireland). Observation in a Reichert-Jung Polyvar microscope operating in differential interference contrast (DIC) mode demonstrated a particle size on the order of 200-300 nanometers had been achieved. The vecuronium bromide concentration in the pH 5.1 dispersion initially assayed at 4.12 mg/mL. After 3 weeks, the vecuronium bromide concentration in the pH 5.1 dispersion assayed at 3.19 mg/ml. In view of the rapid decomposition of vecuronium bromide in simple aqueous solutions, this represents a significant reduction in the decomposition rate of the drug.

Another sample of nearly identical composition was also prepared and assayed for stability. In that experiment, the vecuronium bromide concentration in the pH 5.2 dispersion initially assayed at 3.49 mg/mL. After 4 weeks at 25° C., the vecuronium bromide concentration in the dispersion assayed at 3.41 mg/ml, indicating 97.7% retention of potency; this is a many-fold improvement over the shelf-life of a vecuronium control solution at the same pH and temperature, where potency is reduced to 85% of initial in about 2 weeks.

Example 4

A reversed liquid crystalline, probably hexagonal, phase material containing the quaternary ammonium steroidal neuromuscular blocking agent vecuronium bromide was prepared by first dissolving 0.900 gm of purified phosphatidylcholine, Phospholipon® 90 G (American Lecithin Company, Oxford, Conn.), and 0.300 grams of dimyristoyl phosphatidylglycerol Na/NH4 salt (NOF Corporation, Japan) in 19.247 gm of chloroform (Aldrich Chemical Company, Milwaukee, Wis.). Dimyristoyl phosphatidylglycerol (DMPG) has a pKa of about 3.0, and a carbon number of 34. The solution was transferred to a 100 mL round bottom flask and chloroform was evaporated off by pulling a 5 mBar vacuum (BrandTech Scientific Inc.) for 20 minutes. Then, 0.030 gm of vecuronium bromide (ChemPacific) was dissolved in 0.253 gm of distilled water. Upon dissolution, 0.807 gm of the homogenous PC/DMPG mixture was thoroughly mixed into the vecuronium solution creating a viscous reversed hexagonal phase. Next, a 20% polyethylene glycol 3350 solution was prepared by mixing 2.672 gm of PEG 3350 (Dow Chemical Company, Midland, Mich.) and 10.681 gm of distilled water. An amount, 0.504 gm, of the vecuronium bromide hexagonal phase was dispersed into the 20% PEG 3350 solution and dispersed using a homogenizer (Brinkmann Polytron PT 3000) at 18.8 k RPM for 1 minute. The 1 mg/mL vecuronium bromide dispersion was pH adjusted from 7.3 to 5.8 using 0.1M hydrochloric acid (Aldrich Chemical Company, Milwaukee, Wis.). The dispersion was then filtered using a 0.45 micron PVDF syringe filter (Millipore, Ireland). Observation in a Reichert-Jung Polyvar microscope operating in differential interference contrast (DIC) mode showed mostly 200-500 nm square-shaped particles and some rod-shaped particles 500 nm in length. It is believed that this rod-shaped morphology correlates with at least a portion of the dispersed material being a reversed hexagonal phase.

The vecuronium bromide dispersion was analyzed using a Beckman Coulter DELSA 440SX for Doppler Electrophoretic Light Scattering Analysis, set in zeta potential measurement mode. The dispersion was diluted 1:5 in water to achieve proper detector levels. The resulting zeta potential distribution, using three angles of measurement, shows the distribution centered on −55 mV, which is a strong enough zeta potential to produce a stable dispersion. This strongly negative zeta potential can be traced to the high concentration of DMPG in the particles. Both the DMPG and glycocholate are organic anions with pKa less than 4 and carbon numbers greater than 6.

Example 5

A cubic phase was prepared by mixing a composition where the ratio of tocopherol:PC was approximately 1.09:1, and then adding a 10% solution of vecuronium bromide until this pseudocomponent was between 14.5% and 33% of the composition. Upon incorporating the anionic lipid DMPG (dimyristoylphosphatidylglycerol; pKa approx. 3.0, n=34) at a level of 10% based on the cubic phase, and thus about a 2:1 molar ratio to the cationic drug, a dispersion was produced which had a zeta potential of −25 mV. By further incorporating sodium deoxycholate at 5% of the cubic phase, the zeta potential was increased to −35 mV. This cubic phase was dispersed in a 70 wt % glycerol solution in water. The pH was 6.1.

After 6 weeks of storage at 25° C., the assayed value of vecuronium in this sample was 86% of its initial value, thus indicating that its shelf-life as defined herein was just over 6 weeks. This represents a 6-fold improvement over the control vecuronium solution at this pH and temperature.

Example 6

In this Example, a poloxamer-based cubic phase was dispersed as cationic particles, with the positive charge being due to that of the drug, and benzenesulfonic acid piperidine was added as a stabilizer. In an 8 mL test tube, 0.194 vecuronium bromide (Poli) and 1.814 gm HPLC-grade water were added. The sample was stirred until all vecuronium bromide dissolved. In a second 8 mL test tube, 0.195 gm vecuronium bromide and 1.793 gm linalool (Aldrich) were added. The sample was vortexed until all vecuronium bromide dissolved. In a 30 mL beaker, 1.852 gm 10% vecuronium bromide solution, 1.384 gm 10% vecuronium bromide solution in linalool, and 3.106 gm L122 were added. The sample was stirred until it was homogeneous.

In a beaker, 4.837 gm of benzenesulfonic acid (Aldrich) and 271.60 gm distilled water were added. The sample was stirred until all benzenesulfonic acid was dissolved. The sample was then filtered through a 0.45 micron syringe filter to remove impurities from the benzenesulfonic acid. In a 400 mL beaker, 5.19 gm cubic phase and 254.81 gm benzenesulfonic acid solution were added. The sample was homogenized for two minutes, then microfluidized to disperse the cubic phase. In a 150 mL beaker, 60.00 gm of this dispersion was added. The sample initial pH was 1.92. Piperdine (Aldrich) was added to adjust the sample pH to 5.80.

At a storage temperature of 4° C., the 18-week assay value for this vecuronium formulation of the instant invention was 100% of the initial value.

Example 7

This Example reports an experiment that showed the partitioning of vecuronium into a lipid-based cubic phase over water is significantly increased by the presence of glycocholate (pKa 3.5, 26 carbons), therefore demonstrating the increased effective hydrophobicity of the vecuronium due to its association with glycocholate. It is this hydrophobic milieu that is central to the invention, in limiting the contact between water and the labile group(s) of the drug.

HPLC measurements of vecuronium concentrations in cubic and aqueous phases in equilibrium with each other showed that the cubic-water partition coefficients were very high, and in particular, that $K_{QW}$ can be further increased by the incorporation of a bilayer-bound anionic compound with pKa in the preferred range as discussed herein. The data that were measured are as follows:

Vecuronium in cubic phase without a charged surfactant:
concentration in the cubic phase=10.0 mg/ml
concentration in the aqueous phase=0.006 mg/ml
So, $K_{QW}$=1,667 log $K_{QW}$=+3.2

Vecuronium in cubic phase with a charged surfactant (sodium glycocholate):
Concentration in the cubic phase=10.6 mg/ml
Concentration in the aqueous phase=0.001 mg/ml
So, $K_{QW}$=10,000 log $K_{QW}$=+4

Thus, incorporation of the glycocholate increased the partitioning into the lipid phase by an order of magnitude.

While the invention has been described in terms of its preferred embodiments, those skilled in the art will recognize that the invention can be practiced with modification within the spirit and scope of the appended claims.

Example 8

Formulation #16 from Example 1 above, with 3% saccharin as the organic anion (pKa=2.0, 7 carbons), was tested for compatibility with the marketed Thiopental Sodium product (25 mg/ml sodium thiopental, from Abbott Laboratories). The thiopental formulation was prepared according to the package insert, and mixed with an equal volume of formulation #16, and the mixture examined for signs of precipitation immediately after mixing, and at 2 minutes, 10 minutes, and 4 hours after mixing. As a control, the marketed Esmuron formulation of vecuronium bromide was reconstituted as per instructions, and mixed with the thiopental solution in the same manner.

While extensive precipitation was observed with the Esmuron formulation, in contrast the saccharin-containing formulation of this invention showed only traces of precipitate, even at the 4-hour time point. Thus, this embodiment of the instant invention has the distinct advantage, both from a convenience and a safety perspective, that it is compatible, in direct contact and mixing, with marketed Thiopental Sodium formulations.

Having thus described our invention, what we claim as new and desire to secure by Letters Patent is as follows:

1. A ready to use, safe for injection formulation comprising: vecuronium and saccharin, said vecuronium and said saccharin being dissolved or dispersed in an aqueous solution or an aqueous dispersion, wherein there is a molar excess of said saccharin to quaternary ammonium groups of said vecuronium.

2. The formulation of claim 1 wherein the molar excess of said saccharin to quaternary ammonium groups of said vecuronium is greater than or equal to about 100%.

3. The formulation of claim 1 wherein said molar excess of said saccharin to quaternary ammonium groups of said vecuronium is greater than or equal to about 200%.

4. The formulation of claim 1 wherein said molar excess of said saccharin to quaternary ammonium groups of said vecuronium is greater than or equal to about 800%.

5. The formulation of claim 1 wherein said formulation is substantially free of acetic acid.

* * * * *